(12) United States Patent
Chouinard (10) Patent No.: US 8,414,637 B2
(45) Date of Patent: Apr. 9, 2013

(54) STENT (75) Inventor: Paul F. Chouinard, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 672 days.

(21) Appl. No.: 11/650,050

(22) Filed: Jan. 5, 2007

(65) Prior Publication Data
US 2008/0065193 A1 Mar. 13, 2008

Related U.S. Application Data (60) Provisional application No. 60/843,114, filed on Sep. 8, 2006.

(51) Int. Cl.
*A61F 2/06* (2006.01)

(52) U.S. Cl. ........................................ 623/1.15; 623/1.3

(58) Field of Classification Search ............... 623/1.1, 623/1.15, 1.16, 1.17, 1.35
See application file for complete search history.

(56) References Cited

U.S. PATENT DOCUMENTS

| | | | |
|---|---|---|---|
| 5,741,327 A | 4/1998 | Frantzen |
| 5,755,770 A | 5/1998 | Ravenscroft |
| 5,776,161 A | 7/1998 | Globerman |
| 5,824,046 A | 10/1998 | Smith et al. |
| 5,858,556 A | 1/1999 | Eckert et al. |
| 5,861,027 A | 1/1999 | Trapp |
| 5,876,449 A | 3/1999 | Starck et al. |
| 5,922,020 A | 7/1999 | Klein et al. |
| 5,922,021 A | 7/1999 | Jang |
| 6,013,854 A | 1/2000 | Moriuchi |
| 6,022,374 A | 2/2000 | Imran |
| 6,113,627 A | 9/2000 | Jang |
| 6,193,747 B1 | 2/2001 | von Oepen |
| 6,200,334 B1 | 3/2001 | Jang |
| 6,231,598 B1 | 5/2001 | Berry et al. |
| 6,272,370 B1 | 8/2001 | Gillies et al. |
| 6,280,385 B1 | 8/2001 | Melzer et al. |
| 6,293,966 B1 | 9/2001 | Frantzen |
| 6,299,635 B1 | 10/2001 | Frantzen |
| 6,331,188 B1 | 12/2001 | Lau et al. |
| 6,331,189 B1 | 12/2001 | Wolinsky et al. |
| 6,334,871 B1 | 1/2002 | Dor et al. |
| 6,340,366 B2 | 1/2002 | Wijay |
| 6,340,367 B1 | 1/2002 | Stinson et al. |
| 6,348,065 B1 | 2/2002 | Brown et al. |
| 6,355,058 B1 | 3/2002 | Pacetti et al. |
| 6,361,557 B1 | 3/2002 | Gittings et al. |
| 6,361,759 B1 | 3/2002 | Frayne et al. |
| 6,379,381 B1 | 4/2002 | Hossainy et al. |
| 6,402,777 B1 | 6/2002 | Globerman et al. |

(Continued)

FOREIGN PATENT DOCUMENTS

| | | |
|---|---|---|
| EP | 0801933 | 10/1997 |
| WO | 9925273 | 5/1999 |
| WO | 0132099 | 5/2001 |
| WO | 0158386 | 8/2001 |

*Primary Examiner* — David Isabella
*Assistant Examiner* — Joshua Levine
(74) *Attorney, Agent, or Firm* — Vidas, Arrett & Steinkraus, P.A.

(57) ABSTRACT

A stent having a transitional section positioned between a middle section with different struts lengths and circumferentially non-aligned peaks, and a symmetrical section that has equal strut lengths and circumferentially aligned peaks.

18 Claims, 5 Drawing Sheets

U.S. PATENT DOCUMENTS

| | | |
|---|---|---|
| 6,464,722 B2 | 10/2002 | Israel et al. |
| 6,468,302 B2 | 10/2002 | Cox et al. |
| 6,503,271 B2 | 1/2003 | Duerig et al. |
| 6,524,335 B1 | 2/2003 | Hartley et al. |
| 6,652,579 B1 | 11/2003 | Cox et al. |
| 6,656,215 B1 | 12/2003 | Yanez et al. |
| 6,730,116 B1 | 5/2004 | Wolinsky et al. |
| 7,011,678 B2 | 3/2006 | Tenerz et al. |
| 7,243,408 B2 | 7/2007 | Vietmeier |
| 2001/0029397 A1 | 10/2001 | Thompson |
| 2001/0029398 A1 | 10/2001 | Jadhav |
| 2001/0056298 A1 | 12/2001 | Brown et al. |
| 2002/0007212 A1 | 1/2002 | Brown et al. |
| 2002/0022876 A1 | 2/2002 | Richter et al. |
| 2002/0095208 A1 | 7/2002 | Gregorich et al. |
| 2002/0120322 A1 | 8/2002 | Thompson et al. |
| 2002/0193867 A1 | 12/2002 | Gladdish et al. |
| 2003/0176914 A1 | 9/2003 | Rabkin et al. |
| 2003/0195606 A1 * | 10/2003 | Davidson et al. ............ 623/1.11 |
| 2003/0225448 A1 | 12/2003 | Gerberding |
| 2004/0073290 A1 * | 4/2004 | Chouinard .................... 623/1.15 |
| 2004/0073291 A1 | 4/2004 | Brown et al. |
| 2004/0088039 A1 | 5/2004 | Lee et al. |
| 2004/0111147 A1 | 6/2004 | Rabkin et al. |
| 2004/0267353 A1 | 12/2004 | Gregorich |
| 2005/0015139 A1 | 1/2005 | Brown et al. |
| 2005/0060025 A1 | 3/2005 | Mackiewicz et al. |
| 2005/0149168 A1 | 7/2005 | Gregorich |
| 2005/0172471 A1 * | 8/2005 | Vietmeier ....................... 29/447 |
| 2005/0261760 A1 | 11/2005 | Weber |

\* cited by examiner

STENT

CROSS-REFERENCE TO RELATED APPLICATIONS

This application claims priority from U.S. Application No. 60/843,114, filed on Sep. 8, 2006, the entire contents of which is hereby incorporated by reference.

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use.

2. Description of the Related Art

A stent is a medical device introduced to a body lumen and is well known in the art. Typically, a stent is implanted in a blood vessel at the site of a stenosis or aneurysm endoluminally, i.e. by so-called "minimally-invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent with a transitional section positioned between a middle section with different struts lengths and circumferentially non-aligned peaks and a symmetrical section that has equal strut lengths and circumferentially aligned peaks.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated. As used herein, proximal and distal only identify the relative ends of the stent as shown in the figures and do not necessarily refer to the relative ends of the stent when in use.

Figure 1:
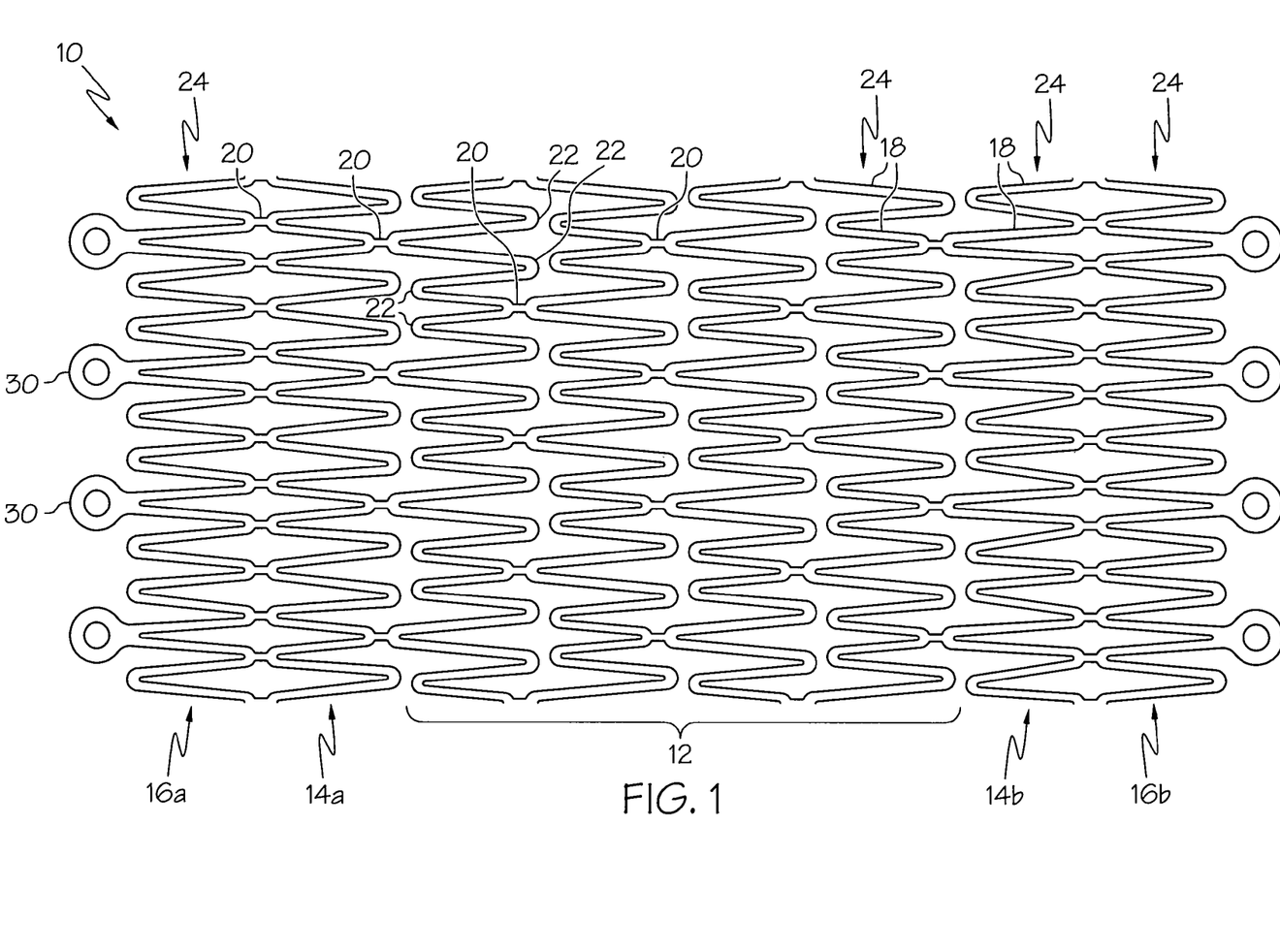
FIG. 1 is a rolled out view of a stent in the unexpanded state.

The stents 10 of the instant application illustrate different means by which a nested stent pattern terminates in a symmetrical pattern. As used in this application, nested refers to stent configurations where circumferential rings have struts of varying lengths so that the peaks and troughs of a circumferential ring are longitudinally staggered, as shown in FIG. 1 and described in greater detail in commonly assigned U.S. patent application Ser. No. 10/269111, entitled Stent with Improved Flexibility, the entire content of which is incorporated by reference herein.

Nested stents 10 that terminate in a symmetrical pattern have an expanded state where the peaks 22 at the proximal and distal ends of the stent 10 are generally longitudinally oriented. Radiopaque markers 30 can be added to these peaks 22 and since the peaks 22 are generally longitudinally oriented, the radiopaque markers 30 extend longitudinally instead of at an angle to the longitudinal axis of the stent 10. The stents 10 of the instant application also maintain the nesting of non-fully connected segments and uniform connector 20 length between stent segments. This results in a nested stent 10 with generally uniform scaffolding and generally uniform stent to lumen ratio along the longitudinal length of the stent 10.

Figure 2:
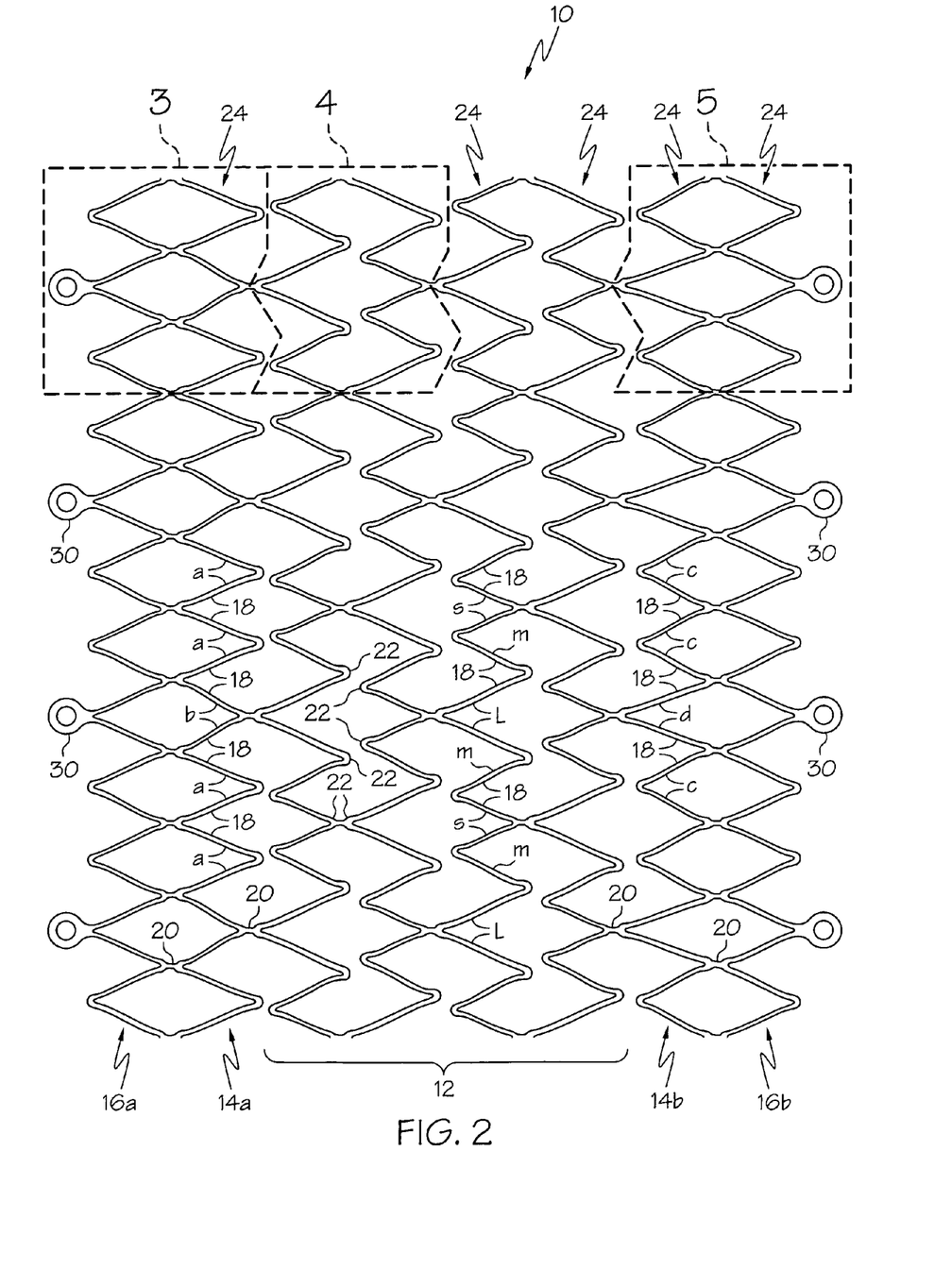
FIG. 2 is a rolled out view of the stent of FIG. 1 in the expanded state.
Figure 3:
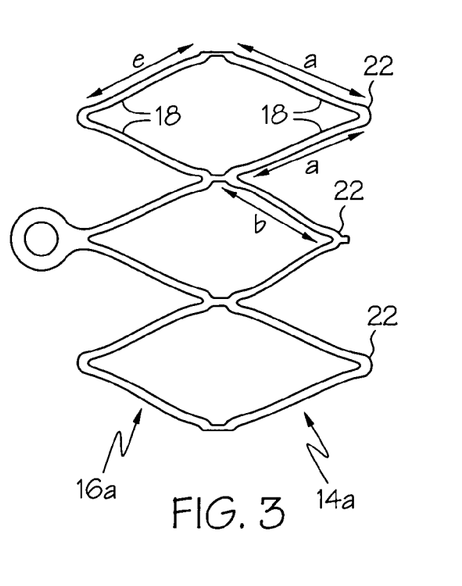
FIG. 3 is an expanded view of a portion of the proximal end section of the stent in FIG. 2.
Figure 6:
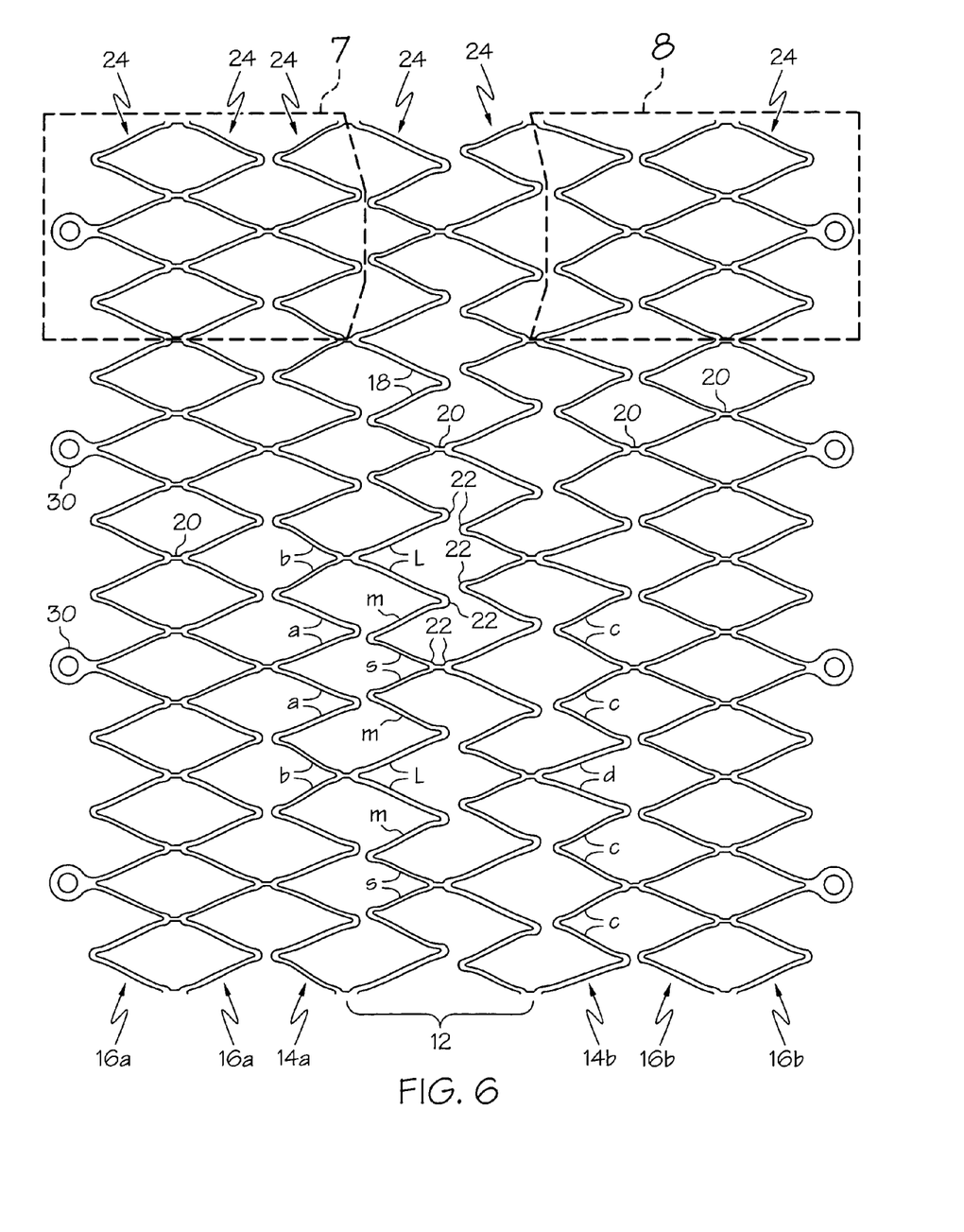
FIG. 6 is a rolled out view of a stent in the expanded state.
Figure 7:
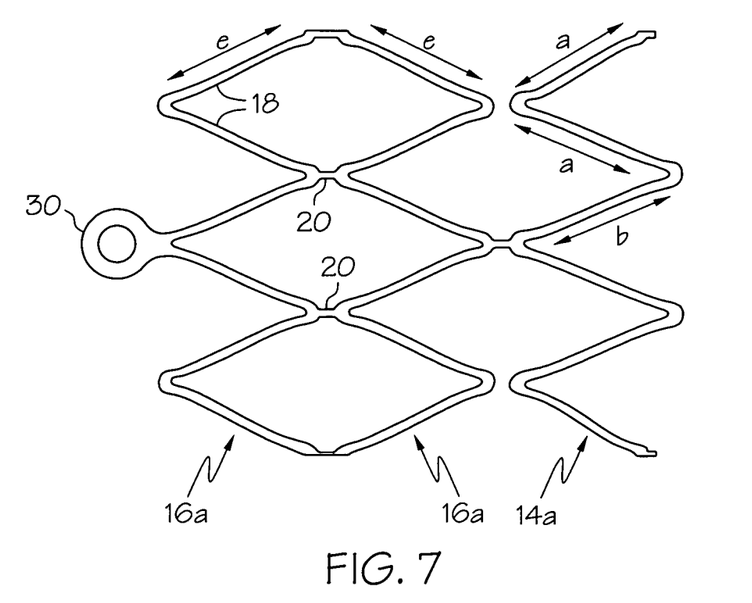
FIG. 7 is an expanded view of a portion of the proximal end section of the stent in FIG. 6.
Figure 8:
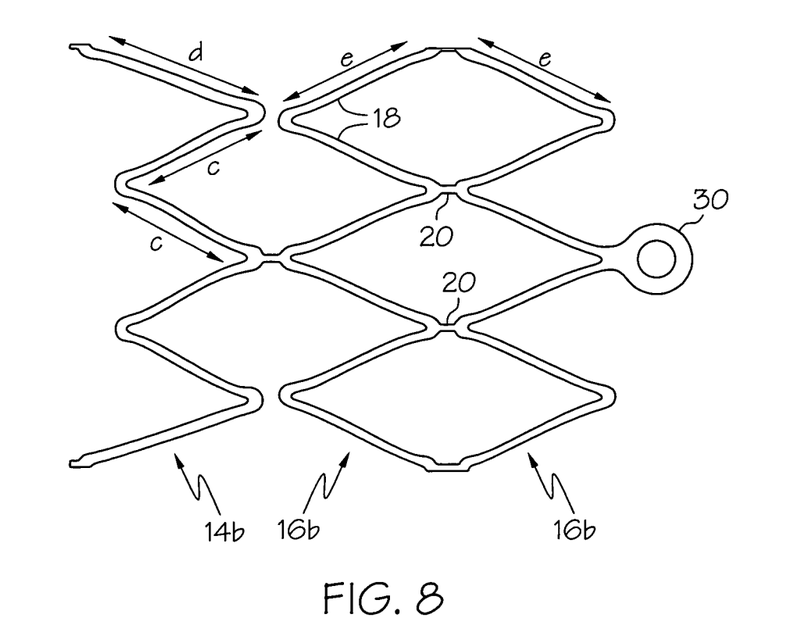
FIG. 8 is an expanded view of a portion of the distal end section of the stent in FIG. 6.

FIGS. 1 and 2 are rolled out views of a nested stent 10 with the stent 10 in FIG. 1 in the unexpanded state while the stent 10 in FIG. 2 is in the expanded state. The stent 10 has five sections: two symmetrical sections 16*a,b*, two transitional sections 14*a,b* and a middle section 12. As illustrated in FIGS. 2 and 6, each section 12,14,16 comprises at least one circumferential ring 24. It is within the scope of the invention for each section 12,14,16 to have one, two, three, four, five, six, seven, eight, nine, ten or more circumferential rings 24 made of a plurality of struts 18 and peaks 22.

The stent 10 also has a plurality of connectors 20. In at least one embodiment, each of the plurality of connectors 20 are peak to peak connectors 20 having the same length. In at least one embodiment, connectors 20 engaging different sections 12,14,16 have different lengths. Connectors 20 engage the proximal symmetrical section 16*a* to the proximal transitional section 14*a*, the proximal transitional section 14*a* to the middle section 12, the middle section 12 to the distal transitional section 14*b* and the distal transitional section 14*b* to the distal symmetrical section 16*b*. In addition, connectors 20 engage adjacent circumferential rings 24 within a section 12,14,16. Although the connectors 20 in the figures are evenly spaced about the circumference of the stent 10, it is within the scope of the invention for the connectors 20 to be unevenly spaced about the circumference of the stent 10.

Figure 4:
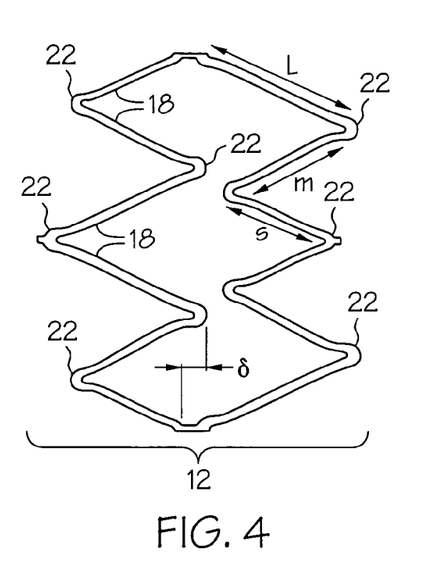
FIG. 4 is an expanded view of a portion of the middle section of the stent in FIG. 2.
Figure 5:
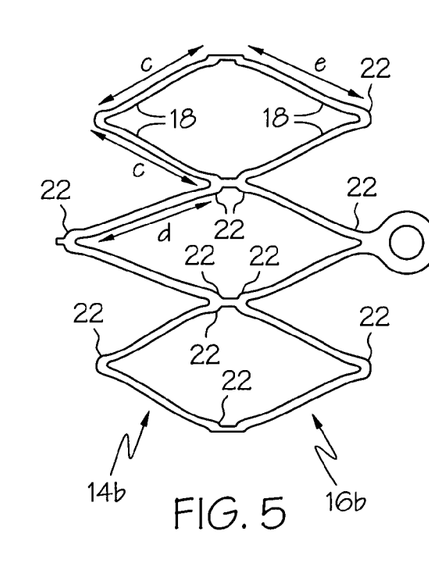
FIG. 5 is an expanded view of a portion of the distal end section of the stent in FIG. 2.

The circumferential rings 24 in the middle section 12 have struts 18 with varying lengths, as illustrated in FIG. 1-2, 6 and the expanded view in FIG. 4. Note that because the struts 18 are different lengths, some of the proximal/distal peaks 22 have a longitudinal position that is different from the circumferentially adjacent peak 22 so that they are longitudinally staggered and some of the proximal/distal peaks 22 are substantially circumferentially aligned with an adjacent circumferential peak 22. As used in this application, peaks 22 are substantially circumferentially aligned if at least a portion of a peak 22 has the same position along the length of the stent 10, a longitudinal position, as a portion of a circumferentially adjacent peak 22 where the peaks 22 are part of the same circumferential ring 24.

Each circumferential ring 24 of the middle section 12 has the following repeating pattern of struts 18: a pair of struts 18 (a pair of struts 18 equals two struts 18), each having a length l; is followed by a strut 18 having a length m; which is followed by a pair of struts 18, each having a length s; which is followed by a strut 18 having a length m; where l, m, and s are different lengths.

In at least one embodiment, length l is greater than length m which is greater than length s. The middle section 12 can be described mathematically as $L_{total}=s+m+l$ and $m-s=l-m=\delta$. $L_{total}$ is a measure of the cumulative length of three adjacent struts with lengths s, m and l. In some embodiments, the $L_{total}$ may include some variance. $\delta$ is the longitudinal distance between the positions of adjacent circumferential peaks in a circumferential ring, as shown in FIG. 4. In some embodiments, the longitudinal distance $\delta$ may include some variance.

In FIGS. 1-2, the middle section 12 has four circumferential rings 24 while the middle section 12 in FIG. 6 has two circumferential rings 24. Note that two peaks 22 separate circumferentially adjacent connectors 20 and that the connectors 20 engaging the same two circumferential rings 24 together are substantially circumferentially aligned. As used in this application, connectors 20 are substantially circumferentially aligned if at least a portion of a connector 20 has the same position along the length of the stent 10, a longitudinal position, as a portion of a circumferentially adjacent connector 22. The connectors 20 engage the peak 22 of the shortest pair of struts 18 in one circumferential ring 24 to the peak 22 of the longest pair of struts 18 in the longitudinally adjacent circumferential ring 24.

The proximal and distal ends of the middle section 12 are engaged to distal and proximal ends of the transitional sections 14*a,b* respectively. Thus, the distal end of the proximal transitional section 14*a* is engaged to the proximal end of the middle section 12 and the proximal end of the distal transitional section 14*b* is engaged to the distal end of the middle section 12. Circumferentially adjacent connectors 20 engaging the middle section 12 to either transitional section 14*a,b* are separated from one another by two peaks 22.

Similar to the middle section 12, the struts 18 forming the circumferential rings 24 of the transitional sections 14*a,b* have varying lengths but the difference between the lengths is not as great as it is in the middle section 12, as is more clearly seen in FIG. 1. Because the struts 18 are different lengths, some of the distal peaks 22 of the proximal transitional section 14*a* have a longitudinal position that is different from the longitudinal position of the circumferentially adjacent peak 22, so that they are longitudinally staggered, and some of the distal peaks 22 are substantially circumferentially aligned to the circumferentially adjacent peak 22. In contrast, all the proximal peaks 22 of the proximal transitional section 14*a* are substantially circumferentially aligned. Similarly, some of the proximal peaks 22 of the distal transitional section 14*b* have a longitudinal position that is different from the longitudinal position of the circumferentially adjacent peak 22, i.e. longitudinally staggered, and some the proximal peaks 22 of the distal transitional section 14*b* substantially circumferentially aligned to the circumferential adjacent peak 22. In addition, all the distal peaks 22 of the distal transitional section 14*b* are substantially circumferentially aligned.

As shown in FIGS. 2 and 6, and in the expanded portions of the stent 10 shown in FIGS. 3, 5, and 7-8, the circumferential ring 24 in the proximal transitional section 14*a* has the following pattern of struts 18: two pairs of struts 18 (four struts 18) having a length a, followed by one pair of struts 18 having a length b, where length a is greater than length b, (a>b). The proximal transitional end section 14*a* can be described mathematically as $L_{total}=2a+b$ and $a-b=\delta$. The circumferential ring 24 in the distal transitional section 14*b* has the same pattern of struts 18: one pairs of struts 18 having a length d, followed by two pair of struts 18 having a length c, where length d is greater than length c, (d>c). The distal transitional section 14*b* of the nested stent 10 can be described mathematically as $L_{total}=2c+d$ and $d-c=\delta$. In at least one embodiment, the $L_{total}$ of the proximal transitional section 14*a*, the $L_{total}$ of the middle section 12 and the $L_{total}$ of the distal transitional section 14*b* are equal to one another.

As shown in FIGS. 2 and 6, for example, the distal end of the proximal symmetrical section 16*a* is engaged to the proximal end of the proximal transitional section 14*a* and the proximal end of the distal symmetrical section 16*b* is engaged to the distal end of the distal transitional section 14*b*. Note that all of the connectors 20 engaging the symmetrical section 16*a,b* to the transitional section 14*a,b*, are substantially circumferentially aligned. This is because the peaks 22 of the transitional sections 14*a,b*, which are adjacent to the symmetrical sections 16*a,b*, are substantially circumferentially aligned. Also note that, in this embodiment, there is a one to one relationship between the number of connectors 20 and the peaks 22 of both the symmetrical section 16*a,b* and the transitional section 14*a,b*, unlike the relationship between the number of connectors 20 and peaks 22 between the transitional section 14a,b and the middle section 12. However, it is within the scope of the invention to have any ratio of peaks and connectors.

The circumferential rings 24 forming the symmetrical sections 16a,b are the outermost circumferential rings 24 of the stent 10. As shown in FIGS. 1-2, 6 and expanded portions shown in FIGS. 3, 5, 7-8, the struts 18 of the symmetrical sections 16a,b all have the same length, length e. Length e can be described mathematically as $e=L_{total}/3$. In FIG. 2, the symmetrical sections 16a,b only have one circumferential ring 24 whereas in FIG. 6, the symmetrical sections 16a,b each have two circumferential rings 24.

As discussed above, the proximal transitional section 14a, distal transitional section 14b and the middle section 12 each have a $L_{total}$. In one embodiment, the $L_{total}$ of each section is the same. Thus, in this embodiment, 2a+b=s+m+l=2c+d. In at least one embodiment, the $L_{total}$ of at least one section is different. In one embodiment, the $L_{total}$ of the middle section 12 is different than the $L_{total}$ of the proximal and distal transitional sections 14a,b, which are the same so that the strut lengths, length e, of the proximal and distal symmetrical sections 16a,b are the same.

Note that some of the proximal peaks 22 of the struts 18 forming the proximal circumferential ring 24 of the proximal symmetrical section 16a and some of the distal peaks 22 of the struts 18 forming the distal circumferential ring 24 of the distal symmetrical section 16b have a radiopaque (RO) marker 30. In this embodiment, the radiopaque marker 30 is in the form of a RO paddle. However, the radiopaque marker 30 can have any form. Because the proximal/distal peaks 22 extend longitudinally when the stent 10 is in an expanded state, the radiopaque markers 30 engaged thereto also extend in a longitudinal direction, instead of at an oblique angle, when the stent 10 is in an expanded state. An oblique angle, as used in this application is any angle between about 0 and about 180 degrees and includes 90 degrees.

Although this embodiment has a total of eight radiopaque markers 30, it is within the scope of the invention for the stent 10 to have one, two, three, four, five, six, seven, eight, nine, ten, eleven, twelve, thirteen, fourteen, fifteen, sixteen or more radiopaque markers 30. Because each radiopaque marker 30 is separated from the adjacent radiopaque marker 30 by two peaks 22, the radiopaque markers 30 are evenly distributed about the circumference of the stent 10. However, it is within the scope of the invention for the radiopaque markers 30 to be unevenly distributed about the circumference of the stent 10.

The following numbered statements characterize the embodiments described above:

1. A stent, the stent comprising:
    a first section, the first section comprising a first circumferential ring and a second circumferential ring, the first circumferential ring comprising a first plurality of struts, the first plurality of struts having a first length, the second circumferential ring comprising a second plurality of struts and a third plurality of struts, the second plurality of struts having a second length, the third plurality of struts having a third length, the sum of two times the second length and the third length equaling a total length, the first length equal to one third the total length;
    a second section, the second section comprising a first circumferential ring, the first circumferential ring comprising a plurality of struts, the plurality of struts comprising a first plurality of struts, a second plurality of struts and a third plurality of struts, the first plurality of struts having a first length, the second plurality of struts having a second length, the third plurality of struts having a third length, the sum of the first length, the second length and the third length equaling a total length;
    a third section, the third section comprising a first circumferential ring and a second circumferential ring, the first circumferential ring comprising a first plurality of struts and a second plurality of struts, the first plurality of struts having a first length, the second plurality of struts having a second length, the second circumferential ring comprising a third plurality of struts, the third plurality of struts having a third length, the sum of two times the first length and the second length equaling a total length, the third length equal to one third the total length; and
    the total lengths of the first, second and third sections being equal.

2. The stent of statement 1, further comprising at least one radiopaque marker.

3. The stent of statement 2, the first circumferential ring of the first section further comprising a plurality of proximal peaks, the second circumferential ring of the third section comprising a plurality of distal peaks, the at least one radiopaque marker engaged to at least one of the plurality of proximal peaks and distal peaks.

4. The stent of statement 3, the radiopaque marker being in the form of a radiopaque paddle.

5. The stent of statement 1, further comprising a plurality of connectors, the plurality of connectors engaging the first section to the second section and the second section to the third section and engaging the circumferential rings of each section to one another.

6. The stent of statement 5, the plurality of connectors being peak to peak connectors.

7. The stent of statement 6, the plurality of connectors being the same length.

The inventive stents may be made from any suitable biocompatible materials including one or more polymers, one or more metals or combinations of polymer(s) and metal(s). Examples of suitable materials include biodegradable or bioabsorbable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In addition to or instead of the use of RO paddles, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising:
  a first section, the first section comprising a first circumferential ring, the first circumferential ring consisting a plurality of first end struts, each first end strut having a first end length where the first end length is the same for each first end strut;
  a second section, the second section comprising a first circumferential ring, the first circumferential ring comprising a plurality of transitional struts, the plurality of transitional struts comprising a first transitional strut and a second transitional strut, the first transitional strut having a first transitional length, the second transitional strut having a second transitional length;
  a plurality of first connectors, the plurality of first connectors engaging the first section and the second section, the plurality of first connectors being substantially circumferentially aligned when the stent is in an unexpanded state; and
  a third section, the third section comprising a first circumferential ring having a circumferential length, the first circumferential ring comprising a plurality of middle struts, the plurality of middle struts comprising a first middle strut, a second middle strut and a third middle strut, the first middle strut having a first middle length, the second middle strut having a second middle length and the third middle strut having a third middle length, the first middle length, the second middle length and the third middle length being different lengths,
    wherein the first middle strut, the second middle strut, and the third middle strut are arranged in a middle pattern, the middle pattern repeating about the entire circumferential length of the first circumferential ring.

2. The stent of claim 1, the first transitional length being different than the second transitional length.

3. The stent of claim 1 further comprising at least one radiopaque marker.

4. The stent of claim 1, the first section further comprising at least one radiopaque marker.

5. The stent of claim 4, the radiopaque marker being in the form of a radiopaque paddle.

6. The stent of claim 5, the radiopaque paddle extending in a longitudinal direction when the stent is in an expanded state.

7. The stent of claim 1, wherein the first section, the second section and the third section define a tubular body, the tubular body having a diameter at the first, second and third sections, the diameter being the same for each section.

8. The stent of claim 1, the first circumferential ring of the first section having a plurality of distal peaks, the first circumferential ring of the second section having a plurality of proximal peaks, the number of peaks forming the plurality of distal peaks the same as the number of peaks forming the plurality of proximal peaks, the plurality of first connectors engaging the distal peaks of the first circumferential ring of the first section and the proximal peaks of the first circumferential ring of the second section.

9. The stent of claim 1, further comprising a plurality of second connectors, the plurality of second connectors engaging the second section to the third section.

10. The stent of claim 9, the plurality of second connectors being peak to peak connectors.

11. The stent of claim 10, the plurality of first and second connectors having the same length.

12. The stent of claim 9, the number of connectors comprising the plurality of first connectors greater than the number of connectors comprising the plurality of second connectors.

13. The stent of claim 1, the first circumferential ring of the second section having a total length equal to two times the sum of the first transitional length plus the second transitional length; the first circumferential ring of the third section having a total length equal to the first middle length plus the sum of the second middle length plus the third middle length, the total length of the first circumferential ring of the second section being equal to the total length of the first circumferential ring of the third section, and the first end length equal to one third the total length.

14. The stent of claim 1, the middle pattern being: first middle strut-first middle strut-second middle strut-third middle strut-third middle strut-second middle strut.

15. The stent of claim 2, the first circumferential ring of the second section having a circumferential length, the first transitional strut and the second transitional strut being arranged in a transitional pattern, the transitional pattern repeating about the entire circumferential length of the first circumferential ring of the second section.

16. The stent of claim 15, the transitional pattern being: first transitional strut-first transitional strut-first transitional strut-first transitional strut-second transitional strut-second transitional strut.

17. A stent, the stent comprising:
- a first section, the first section comprising a first circumferential ring, the first circumferential ring consisting of a plurality of first end struts, each of the plurality of first end struts having a first end length, each first end strut having the same first end length;
- a second section, the second section comprising a first circumferential ring, the first circumferential ring comprising a plurality of transitional struts, each transitional strut having a first end, the plurality of transitional struts comprising a first transitional strut and a second transitional strut, the first transitional strut having a first transitional length, the second transitional strut having a second transitional length different than the first transitional length, all of the first ends being substantially circumferentially aligned;
- a plurality of first connectors, the plurality of first connectors engaging the first section and the second section, the plurality of first connectors being substantially circumferentially aligned when the stent is in an unexpanded state; and
- a third section, the third section comprising a first circumferential ring, the first circumferential ring comprising a plurality of middle struts, the plurality of middle struts comprising a first middle strut, a second middle strut and a third middle strut, the first middle strut having a first middle length, the second middle strut having a second middle length and the third middle strut having a third middle length, the first, second, and third middle lengths being different lengths, each middle strut having a first end and a second end, some of the first ends being circumferentially aligned with an adjacent first end and some of the second ends being circumferentially aligned with an adjacent second end;
- a plurality of second connectors, the plurality of second connectors engaging the second section and the third section.

18. A stent, the stent having a circumference and comprising a plurality of first end struts, a plurality of first transitional struts, a plurality of second transitional struts, a plurality of first middle struts, a plurality of second middle struts, a plurality of third middle struts, a plurality of first connectors and a plurality of second connectors;
- the plurality of first end struts forming at least one end circumferential ring extending about the entire circumference of the stent, each first end strut having a first length that is the same for each first end strut;
- the plurality of first and second transitional struts forming at least one transitional circumferential ring extending about the entire circumference of the stent, each first transitional strut having a first length and each second transitional strut having a second length, the first and second transitional struts being arranged in a pattern, the pattern being repeated about the entire circumference of the stent;
- the plurality of first connectors engaging an end circumferential ring to a transitional circumferential ring;
- the plurality of first, second, and third middle struts forming at least one middle circumferential ring extending about the entire circumference of the stent, each first middle strut having a first length, each second middle strut having a second length, and each third middle strut having a third length, the first, second and third lengths being different lengths, the first, second and third middle struts being arranged in a pattern, the pattern being repeated about the entire circumference of the stent; and
- the plurality of second connectors engaging a transitional circumferential ring to a middle circumferential ring.

* * * * *